United States Patent [19]

Chu

[11] 4,259,537

[45] Mar. 31, 1981

[54] SHAPE SELECTIVE REACTIONS WITH GROUP VIA MODIFIED ZEOLITE CATALYSTS

[75] Inventor: Chin-Chiun Chu, North Brunswick, N.J.

[73] Assignee: Mobil Oil Corporation, Fairfax, Va.

[21] Appl. No.: 130,953

[22] Filed: Mar. 17, 1980

[51] Int. Cl.$^3$ .......................... C07C 2/68; C07C 5/22; C07C 5/52
[52] U.S. Cl. .................................. 585/467; 585/474; 585/475
[58] Field of Search ..................... 585/467, 474, 475

[56] References Cited

U.S. PATENT DOCUMENTS

| | | | |
|---|---|---|---|
| 3,965,208 | 6/1976 | Butter et al. | 585/454 |
| 3,972,832 | 8/1976 | Butter et al. | 585/514 |
| 3,979,472 | 9/1976 | Butter | 585/408 |
| 4,002,697 | 1/1977 | Chen | 585/467 |
| 4,034,053 | 7/1977 | Kaeding et al. | 585/467 |
| 4,052,476 | 10/1977 | Morrison | 585/475 |
| 4,067,920 | 1/1978 | Kaeding | 585/467 |
| 4,101,597 | 7/1978 | Breckenridge | 585/475 |
| 4,117,026 | 9/1978 | Haao et al. | 585/475 |
| 4,128,592 | 12/1978 | Kaeding | 585/467 |
| 4,137,195 | 1/1979 | Chu | 252/437 |

*Primary Examiner*—Curtis R. Davis
*Attorney, Agent, or Firm*—Charles A. Huggett; Ronald J. Cier

[57] ABSTRACT

A process for the conversion of aromatic compounds to dialkylbenzene compounds rich in the 1,4-dialkylbenzene isomer. The reaction is carried out in the presence of a particular type of zeolite catalyst having a silica to alumina mole ratio of at least 12 and a constraint index of about 1–12, said catalyst having been modified by treatment with compounds of the Group VIA metals (Cr, Mo, W), and optionally phosphorus, to deposit a minor proportion of such elements on the zeolite.

26 Claims, No Drawings

SHAPE SELECTIVE REACTIONS WITH GROUP VIA MODIFIED ZEOLITE CATALYSTS

BACKGROUND OF THE INVENTION

1. Field of the Invention

The invention disclosed herein relates to the production of dialkylbenzene compounds utilizing a modified crystalline zeolite catalyst to yield a product mixture in which the 1,4-dialkylbenzene isomer is substantially in excess of its normal equilibrium concentration.

2. Description of the Prior Art

The disproportionation of aromatic hydrocarbons in the presence of zeolite catalysts has been described by Grandio et al. in the OIL AND GAS JOURNAL, Vol. 69, Number 48(1971).

U.S. Pat. Nos. 3,126,422; 3,413,374; 3,598,878; 3,598,879 and 3,607,961 show vapor-phase disproportionation of toluene over various catalysts.

In these prior art processes, the dimethylbenzene product produced has the equilibrium composition of approximately 24 percent of 1,4-, 54 percent of 1,3- and 22 percent of 1,2-isomer. Of the dimethylbenzene isomers, 1,3-dimethylbenzene is normally the least desired product, with 1,2- and 1,4-dimethylbenzene being the more useful products. 1,4-Dimethylbenzene is of particular value, being useful in the manufacture of terephthalic acid which is an intermediate in the manufacture of synthetic fibers such as "Dacron". Mixtures of dimethylbenzene isomers, either alone or in further admixture with ethylbenzene, have previously been separated by expensive superfractionation and multistage refrigeration steps. Such process, as will be realized, involves high operation costs and has a limited yield.

Various modified zeolite catalysts have been developed to alkylate or disproportionate toluene with a greater or lesser degree of selectivity to 1,4-dimethylbenzene isomer. Hence, U.S. Pat. Nos. 3,972,832, 4,034,053, 4,128,592 and 4,137,195 disclose particular zeolite catalysts which have been treated with compounds of phosphorus and/or magnesium. Boron-containing zeolites are shown in U.S. Pat. No. 4,067,920 and antimony-containing zeolites in U.S. Pat. No. 3,979,472. Similarly, U.S. Pat. Nos. 3,965,208 and 4,117,026 disclose other modified zeolites useful for shape selective reactions.

While the above-noted prior art is considered of interest in connection with the subject matter of the present invention, the conversion process described herein, utilizing a crystalline zeolite catalyst of specified characteristics which has undergone the particular treatment disclosed, has not, insofar as is known, been previously described.

SUMMARY OF THE INVENTION

In accordance with the present invention, there has now been discovered a novel process for conversion of organic compounds (e.g. hydrocarbon compounds) in the presence of a particular type of modified zeolite catalyst. An especially advantageous element of the invention comprises the selective production of the 1,4-isomer of dialkylated benzene compounds. The process involves contacting an alkylated aromatic compound, either alone or in admixture with a suitable alkylating agent such as methanol or ethylene, with particular type of modified crystalline zeolite catalyst and under suitable conversion conditions to effect disproportionation or transalkylation of alkylbenzene compounds or alkylation of aromatic compounds to selectively produce the 1,4-dialkylbenzene isomer in excess of its normal equilibrium concentration.

The particular type of crystalline zeolite catalysts utilized herein are zeolite materials having a silica to alumina ratio of at least about 12, a constraint index within the approximate range of 1 to 12 and which have been modified by initial treatment with a compound derived from one or more of the elements of Group VIA of the Periodic Table of Elements (i.e. Cr, Mo and W) to yield a composite containing a minor proportion of an oxide of such element. In addition to treatment of the catalyst with the chromium, molybdenum or tungsten containing compound, the zeolite may also be treated with a phosphorus-containing compound to deposit a minor proportion of an oxide of phosphorus thereon in addition to the oxide of the Group VIA metal.

An embodiment of the disclosed invention is a process for the alkylation of aromatic compounds, in the presence of the herein described modified zeolite catalysts, with selective production of the 1,4-dialkylbenzene isomer in preference to the 1,2- and 1,3-isomers thereof. Especially preferred embodiments involve the selective production of 1,4-dimethylbenzene from toluene and methanol and 1-ethyl-4-methylbenzene from toluene and ethylene.

Another embodiment contemplates the selective disproportionation or transalkylation of alkylbenzene and polyalkylbenzene compounds in the presence of the disclosed catalysts, thereby yielding 1,4-disubstituted benzenes in excess of their normal equilibrium concentration. For example, under appropriate conditions of temperature and pressure, toluene will disproportionate in the presence of these catalysts to produce benzene and dimethylbenzenes rich in the desirable 1,4-isomer.

DESCRIPTION OF SPECIFIC EMBODIMENTS

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having substantially higher silica/alumina ratios, e.g. 1600 and above. In addition, zeolites as otherwise characterized herein but which are substantially free of aluminum, that is, zeolites having silica to alumina mole ratios of up to infinity, are found to be useful and even preferable in some instances. Such "high silica" or "highly siliceous" zeolites are intended to be included within this description. Also to be included within this definition are substantially pure silica analogs of the useful zeolites described herein, that is to say, those zeolites having no measurable amount of aluminum (silica to alumina mole ratio of infinity) but which otherwise emobdy the characteristics disclosed.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10} (\text{fraction of hexane remaining})}{\log_{10} (\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. Nos. 3,702,886 and Re 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

(0–15)RN: (0–1.5)$M_{2/n}$O: (0–2)$Al_2O_3$: (100)$SiO_2$ wherein:
M is at least one cation having a valence n; and
RN is a $C_1$–$C_{20}$ organic compound having at least one amine functional group of $pK_a \geq 7$.

It is recognized that, particularly when the composition contains tetrahedral, framework aluminum, a fraction of the amine functional groups may be protonated. The doubly protonated form, in conventional notation, would be $(RNH)_2O$ and is equivalent in stoichiometry to $2RN+H_2O$.

The characteristic X-ray diffraction pattern of the synthetic zeolite ZSM-48 has the following significant lines:

| Characteristic Lines of ZSM-48 | |
|---|---|
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$ is the intensity of the strongest line or peak, and d (obs.), the interplanar spacing in A, corresponding to the recorded lines, were calculated. In the foregoing table the relative intensities are given in terms of the symbols W=weak, VS=very strong and W-S=weak-to-strong. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | | BROAD | PREFERRED |
|---|---|---|---|
| $Al_2O_3/SiO_2$ | = | 0 to 0.02 | 0 to 0.01 |
| $Na/SiO_2$ | = | 0 to 2 | 0.1 to 1.0 |
| $RN/SiO_2$ | = | 0.01 to 2.0 | 0.05 to 1.0 |
| $OH^-/SiO_2$ | = | 0 to 0.25 | 0 to 0.1 |
| $H_2/SiO_2$ | = | 10 to 100 | 20 to 70 |
| $H^+(added)/SiO_2$ | = | 0 to 0.2 | 0 to 0.05 | wherein RN is a $C_1$–$C_{20}$ organic compound having amine functional group of $pK_a \geq 7$. The mixture is maintained at 80°–250° C. until crystals of the material are formed. $H^+$(added) is moles acid added in excess of the moles of hydroxide added. In calculating $H^+$(added) and OH values, the term acid ($H^+$) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor, at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, ammonium sulfate, sodium aluminate, aluminum oxide, or aluminum itself. RN is a $C_1$–$C_{20}$ organic compound containing at least one amine functional group of $pK_a \geq 7$, as defined above, and includes such compounds as $C_3$–$C_{18}$ primary, secondary, and tertiary amines, cyclic amine (such as piperidine, pyrrolidine and piperazine), and polyamines such as $NH_2-C_nH_{2n}-NH_2$ wherein n is 4–12.

The original cations can be subsequently replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38, and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The above crystalline zeolites employed are, in accordance with the present invention, contacted with a solution of one or more compounds of the elements of Grop VIA of the Periodic Chart of the Elements. The Periodic Chart referred to herein is that version officially approved by the United States National Bureau of Standards (NBS) and the International Union of Pure and Applied Chemists (IUPAC), the elements of Group VIA being chromium (Cr), molybdenum (Mo) and tungsten or wolfram (W).

Solutions of such compounds may be in any suitable solvent which is inert with respect to the metal-containing compound and the zeolite. Non-limiting examples of some suitable solvents include water, aromatic and aliphatic hydrocarbons, alcohols, organic acids (such as acetic acid, formic acid, propionic acid and so forth), and inorganic acids (such as hydrochloric acid, sulfuric acid and nitric acid). Other commonly available solvents such as halogenated hydrocarbons, ketones, ethers, etc. may also be useful to dissolve some metal compounds or complexes. Generally, the most useful solvent will be found to be water. However, the solvent of choice for any particular compound will, of course, be determined by the nature of that compound and for that reason the foregoing list should not be considered exhaustive of all of the suitable possibilities.

Representative chromium-containing compounds include chromium acetate, chromium bromide, chromium chloride, chromium fluoride, chromium iodide, chromium nitrate, chromium oxychloride, chromium acetylacetonate, chromium oxalate, chromium sulfide, chromium tartarate, hexammine chromium chloride, chromium oxide, chromium sulfide and chromium carbonate. This listing is not to be taken as encompassing all of the utilizable chromium-containing compounds. It is merely intended to be illustrative of some of the representative metal compounds which those in the art will find useful in practicing the disclosed invention. The knowledgeable reader will readily appreciate that there are numerous other known chromium salts and complexes which would prove useful herein to provide solutions containing chromium suitable for combination with the zeolite in the manner hereinafter described.

Reaction of the zeolite with the treating chromium compound is effected by contacting the zeolite with such compound. Where the treating compound is a liquid, such compound can be in solution in a solvent at the time contact with the zeolite is effected. Any solvent relatively inert with respect to the treating chromium compound and the zeolite may be employed. Suitable solvents include water and aliphatic, aromatic or alcoholic liquid. The treating compound may also be used without a solvent, i.e. may be used as a neat liquid. Where the treating compound is in the gaseous phase, it can be used by itself or in admixture with a gaseous diluent relatively inert to the treating compound and the zeolite (such as helium or nitrogen) or with an organic solvent such as octane or toluene. Heating of the chromium compound impregnated catalyst subsequent to preparation and prior to use is preferred, and such heating can be carried out in the presence of oxygen—for example, in air. Although heating may be carried out at a temperature of about 150° C., higher temperatures, e.g. up to about 500° C., are preferred. Heating is generally carried out for 1–5 hours but may be extended to 24 hours or longer. While heating temperatures above about 500° C. may be employed, they are generally not necessary, and at temperatures of about 1000° C. the crystal structure of the zeolite tends to deteriorate. After heating in air at elevated temperatures, and without being limited by any theoretical considerations, it is contemplated that the chromium is actually present in the zeolite in an oxidized state, such as $Cr_2O_3$.

The amount of chromium oxide incorporated in the zeolite should be at least about 0.25 percent by weight. However, it is preferred that the amount be at least about 1.0 percent by weight, particularly when the zeolite is combined with a binder, e.g. 35 weight percent of alumina. The amount of chromium oxide can be as high as about 30 percent by weight or more, depending on the amount and type of binder present. Preferably, the amount of chromium oxide added to the zeolite will be between about 1.0 and about 20 percent by weight.

The amount of chromium incorporated with the zeolite by reaction with elemental chromium or chromium-containing compound will depend upon several factors. One of these is the reaction time, i.e., the time that the zeolite and the chromium-containing source are maintained in contact with each other. With greater reaction times, all other factors being equal, a greater amount of metal is incorporated with the zeolite. Other factors upon which the amount of chromium incorporated with the zeolite is dependent include reaction temperature, concentration of the treating compound in the reaction mixture, the degree to which the zeolite has been dried prior to reaction with the metal-containing compound, the conditions of drying of the zeolite after reaction with the treating compound, and the amount and type of binder incorporated with the zeolite.

Oxides of molybdenum are also effective modifying components for imparting the desirable shape selective activity to the particular type of zeolites disclosed. Examples of representative molybdenum-containing compounds suitable for deposition of that metal on the zeolite include molybdenum oxide, molybdenum dioxydichloride, molybdenum oxytetrachloride, molybdenum oxychloride acid and ammonium molybdate. As discussed above with respect to the illustrative listing of chromium compounds, the foregoing is not to be considered as an exhaustive list of the utilizable molybdenum salts and complexes. There are numerous molybdenum compounds which the foregoing will suggest to those skilled in the art as being suitable for providing the molybdenum-containing solutions for treatment of the zeolite as hereinafter described.

Reaction of the zeolite with the molybdenum compounds is accomplished in substantially the same way as that recited above with respect to the chromium-containing compounds. Without being limited by any theoretical considerations, it is contemplated that the molybdenum is likewise in an oxidized state, such as $MoO_3$.

The amount of molybdenum oxide incorporated in the zeolite should be at least about 0.25 percent by weight. However, it is preferred tht the amount be at least about 1.0 percent by weight, particularly when the zeolite is combined with a binder, e.g. 35 weight percent of alumina. The amount of molybdenum oxide can be as high as about 40 percent by weight or more depending on the amount and type of binder present. Preferably, the amount of molybdenum oxide added to the zeolite will be between about 1 and about 30 percent by weight.

Oxides of tungsten may also be employed as a modifying component. The tungsten oxide is contemplated as being present as $WO_3$ alone or in combination with other compounds of tungsten in an oxidized state. In all instances, regardless of the particular state of oxidation of the tungsten, its content with respect to the zeolite is computed as if it were present as $WO_3$. Generally, the amount of $WO_3$ in the composite catalyst will be about 1.0 and about 40 weight percent, and preferably between about 2 and about 30 weight percent, based on the weight of the composite. Reaction of the zeolite with the tungsten-containing compound is carried out as described above with respect to the treatment with compounds of the element chromium. Examples of tungsten compounds which may be utilized include, but are not limited to, tungsten oxide, tungsten sulfide, tungsten carbonate, tungsten oxydichloride, tungsten trisulfide, ortho tungstic acid and meta tungstic acid. Again, this listing is not intended to be exhaustive, but rather suggestive to those of skill in the art as to the kinds of metal-containing compounds useful for treating the zeolites as herein described.

In some instances, it may be desirable to modify the crystalline zeolites by combining therewith two or more of the specified metal oxides. Thus, the zeolite may be modified by prior combination therewith of oxides of chromium and molybdenum, oxides of chromium and tungsten, oxides of molybdenum and tungsten, or even oxides of all three elements. When such modification technique is employed, the respective oxides may be deposited on the zeolite either sequentially or from a solution containing suitable compounds of the elements, the oxides of which are to be combined with the zeolite. The amounts of oxides present in such instance are in the same range as specified above for the individual oxides, with the overall added oxide content being between about 1.0 and about 40 weight percent of the composite.

A further embodiment of this invention includes additional modification of the above metal oxide—zeolite composites with phosphorus, whereby from about 0.25 weight percent to about 30 weight percent of an oxide of phosphorus, calculated as $P_2O_5$, is combined with the zeolite. The preferred amount of phosphorus oxide will be between about 1.0 weight percent and about 25 weight percent, based on the weight of the treated zeolite. The phosphorus treatment of the zeolite catalyst will preferably be carried out before the previously described modification with Group VIA metals. Reaction of the zeolite compound with the phosphorus-containing compound is carried out essentially as described above with respect to the metal-containing compounds and it is preferred that the total amount of oxides combined with the zeolite, i.e. the phosphorus oxides plus the metal oxides, fall within the approximate range of 2 percent to 35 percent by weight, based on the weight of the treated zeolite.

Representtive phosphorus-containing compounds which may be used include derivatives of groups represented by $PX_3$, $RPX_2$, $R_2PX$, $R_3P$, $X_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(SX)_2$, $ROP(OX)_2$, $RSP(SX)_2$, $(RS)_2PSP(SR)_2$, and $(RO_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)(OX)$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkylalkylphosphinite, $(R)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphite. The alkyl groups in the mentioned compounds contain from one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PCl$, dialkylphosphinochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)(R)P(S)Cl$ and $R_2P(S)Cl$.

Preferred phosphorous-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphonic acid, diethylchlorothiophosphate, methyl acid phosphate and other alcohol-$P_2O_5$ reaction products.

Particularly preferred are ammonium phosphates, including ammonium hydrogen phosphate, $(NH_4)_2HPO_4$, and ammonium dihydrogen phosphate, $NH_4H_2PO_4$.

Still another modifying treatment entails steaming of the zeolite by contact with an atmosphere containing from about 5 to about 100 percent steam at a temperature of from about 250° to about 1000° C. for a period of between about 15 minutes and about 100 hours and under pressures ranging from sub-atmospheric to several hundred atmospheres. Preferably, steam treatment is effected at a temperature of between about 400° C. and about 700° C. for a period of between about 1 and about 24 hours.

Another modifying treatment involves precoking of the catalyst to deposit a coating of between about 2 and about 75, and preferably between about 15 and about 75 weight percent of the coke thereon. Precoking can be accomplished by contacting the catalyst with a hydrocarbon charge, e.g. toluene, under high severity conditions or alternatively at a reduced hydrogen to hydrocarbon concentration, i.e. 0 to 1 mole ratio of hydrogen to hydrocarbon, for a sufficient time to deposit the desired amount of coke thereon.

It is also contemplated that a combination of steaming and precoking of the catalyst under the above conditions may be employed to suitably modify the crystalline zeolite catalyst.

Alkylation of aromatic compounds in the presence of the above-described catalyst is effected by contact of the aromatic with an alkylating agent. A particularly preferred embodiment involves the alkylation of toluene wherein the alkylating agents employed comprise methanol or other well known methylating agents or ethylene. The reaction is carried out at a temperature of between about 250° C. and about 750° C., preferably beween about 300° C. and 650° C. At higher temperatures, the zeolites of high silica/alumina ratio are preferred. For example, ZSM-5 having $SiO_2/Al_2O_3$ ratio of 30 and upwards is exceptionally stable at high temperatures. The reaction generally takes place at atmospheric pressure, but pressures within the approximate range of $10^5$ N/m$^2$ to $10^7$ N/m$^2$ (1–100 atmospheres) may be employed.

Some non-limiting examples of suitable alkylating agents would include olefins such as, for example, ethylene, propylene, butene, decene and dodecene, as well as formaldehyde, alkyl halides and alcohols, the alkyl portion thereof having from 1 to 16 carbon atoms. Numerous other aliphatic compounds having at least one reactive alkyl radical may be utilized as alkylating agents.

Aromatic compounds which may be selectively alkylated as described herein would include any alkylatable aromatic hydrocarbon such as, for example, benzene, ethylbenzene, toluene, dimethylbenzenes, methylethylbenzenes, propylbenzene, isopropylbenzene, isopropylmethylbenzenes, or substantially any mono- or di-substituted benzenes which are alkylatable in the 4-position of the aromatic ring.

The molar ratio of alkylating agent to aromatic compound is generally between about 0.05 and about 5. For instance, when methanol is employed as the methylating agent and toluene is the aromatic, a suitable molar ratio of methanol to toluene has been found to be approximately 1–0.1 moles of methanol per mole of toluene. Reaction is suitably accomplished utilizing a feed weight hourly space velocity (WHSV) of between about 1 and about 1000, and preferably between about 1 and about 200. The reaction product, consisting predominantly of the 1,4-dialkyl isomer, e.g. 1,4-dimethylbenzene, 1-ethyl-4-methylbenzene, etc., or a mixture of the 1,4- and 1,2-isomers together with comparatively smaller amounts of 1,3-dialkylbenzene isomer, may be separated by any suitable means. Such means may include, for example, passing the reaction product stream through a water condenser and subsequently passing the organic phase through a column in which chromatographic separation of the aromatic isomers is accomplished.

When transalkylation is to be accomplished, transalkylating agents are alkyl or polyalkyl aromatic hydrocarbons wherein alkyl may be composed of from 1 to about 5 carbon atoms, such as, for example, toluene, xylene, trimethylbenzene, triethylbenzene, dimethylethylbenzene, ethylbenzene, diethylbenzene, ethyltoluene, and so forth.

Another aspect of this invention involves the selective disproportionation of alkylated aromatic compounds to produce dialkylbenzenes wherein the yield of 1,4-dialkyl isomer is in excess of the normal equilibrium concentration. In this context, it should be noted that disproportionation is a special case of transalkylation in which the alkylatable hydrocarbon and the transalkylating agent are the same compound, for example when toluene serves as the donor and acceptor of a transferred methyl group to produce benzene and xylene.

The transalkylation and disproportionation reactions are carried out by contacting the alkylbenzene reactants with the above-described modified zeolite catalyst at a temperature of between about 250° C. and 750° C. at a pressure of between atmospheric ($10^5$ N/m$^2$) and about 100 atmospheres ($10^7$ N/m$^2$). The reactant feed WHSV will normally fall within the range of about 0.1 to about 50. Preferred alkylated aromatic compounds suitable for utilization in the disproportation embodiment comprise toluene, ethylbenzene, propylbenzene or substantially any mono-substituted alkylbenzene. These aromatic compounds are selectively converted to, respectively, 1,4-dimethylbenzene, or other 1,4-dialkylbenzene, as appropriate, with benzene being a primary side product in each instance. The product is recovered from the reactor effluent by conventional means, such as distillation to remove the desired products of benzene and dialkylbenzene, and any unreacted aromatic component is recycled for further reaction.

The hydrocarbon conversion processes described herein may be carried out as a batch type, semi-continuous or continuous operation utilizing a fixed or moving bed catalyst system. The catalyst after use in a moving bed reactor is conducted to a regeneration zone wherein coke is burned from the catalyst in an oxygen-containing atmosphere, e.g. air, at an elevated temperature, after which the regenerated catalyst is recycled to the conversion zone for further contact with the charge stock. In a fixed bed reactor, regeneration is carried out in a conventional manner where an inert gas containing a small amount of oxygen (0.5–2%) is used to burn the coke in a controlled manner so as to limit the temperature to a maximum of around 500°–550° C.

The following examples will serve to illustrate certain specific embodiments of the hereindisclosed invention. These examples should not, however, be construed as limiting the scope of the novel invention as there are many variations which may be made thereon without departing from the spirit of the disclosed invention, as those of skill in the art will recognize.

EXAMPLE 1A

[Alkylation reaction with unmodified ZSM-5]

A five gram portion of HZSM-5, containing 35 wt.% alumina binder and having a $SiO_2/Al_2O_3=70$, was placed in a Quartz reactor maintained at the desired temperature. A toluene/methanol mixture in a 4 to 1 molar ratio, was passed thru the reactor at a weight hourly space velocity of 10. The results obtained under varying temperature conditions are shown below.

| Temperature °C. | Percent toluene conversion | Percent para-xylene in xylenes |
| --- | --- | --- |
| 350 | 47.2 | 24.8 |
| 400 | 58.0 | 24.4 |
| 450 | 68.0 | 24.3 |
| 500 | 87.6 | 24.2 |

EXAMPLE 1B

In a similar manner to that of Example 1A, toluene was alkylated with ethylene by passing toluene and ethylene at weight hourly space velocity at 7.0 and 0.5, respectively, over the HZSM-5 catalyst. The results at various temperature are shown below.

| Temperature °C. | Percent toluene conversion | Percent para-ethyltoluene in ethyltoluene |
| --- | --- | --- |
| 400 | 76.4 | 29.9 |
| 425 | 76.4 | 29.9 |
| 450 | 79.0 | 29.6 |

EXAMPLE 2

[Disproportionation reaction with unmodified ZSM-5]

Unmodified ZSM-5, containing 35 wt.% alumina binder and having a $SiO_2/Al_2O_3=70$, was used for disproportionating toluene by passing the same over 6.0 grams of the catalyst at a weight hourly space velocity of 3.5–3.6 at temperatures between 450° C. and 600° C. The conditions and results are summarized in Table below.

| Temperature °C. | WHSV | Toluene conversion mole % | wt.% Selectivity, Benzene | wt.% Selectivity, Xylenes | % para in xylene products |
| --- | --- | --- | --- | --- | --- |
| 450 | 3.6 | 7.4 | 43.5 | 55.5 | 24.7 |
| 500 | 3.5 | 20.5 | 44.6 | 53.8 | 24.5 |
| 550 | 3.5 | 38.8 | 48.0 | 48.8 | 24.2 |
| 600 | 3.5 | 49.2 | 54.4 | 41.7 | 24.1 |

EXAMPLE 3

[Preparation of Mo-ZSM-5]

A 3.0 g portion of HZSM-5, having a $SiO_2/Al_2O_3=70$, was added to a solution 5.0 g $(NH_4)_6Mo_7O_{24}\cdot4H_2O$ in 60 ml water at 50°–60° C. and the mixture was maintained at 50°–60° C. for 4 hours. After filtration and drying at 90° C. for 3 hours, it was calcined at 500° C. for 5 hours to yield 5.2 g Mo-ZSM-5. The Mo content was calculated to be 28%.

EXAMPLE 4

[Alkylation reaction with the Mo-modified zeolite]

Alkylation of toluene with methanol was carried out by passing a toluene/methanol mixture in a molar ratio of 4/1 through 1.1 g of the catalyst of Example 3. The feed WHSV was 10 and the reactor temperature 600° C. Conversion of toluene was 86% and the yield of p-xylene in xylene products was 28.5%.

EXAMPLE 5

[Preparation of W-ZSM-5]

To a solution of 5.0 g $(NH_4)_6H_2W_{12}O_{40}$ in 5 ml of water at 80° C. was added 3.0 g HZSM-5 [$SiO_2/Al_2O_3=70$]. The mixture was maintained at 80°–90° C. for 3 hours. After filtration and drying at 90° C. for 1.5 hours, the catalyst was calcined at 500° C. for 2 hours to yield 4.6 g of W-ZSM-5. The tungsten content was analyzed to be 27.9%.

EXAMPLE 6

[Alkylation reaction with the W-modified zeolite]

Alkylation of toluene with methanol was carried out by passing a toluene/methanol mixture in a molar ratio of 4/1 at a feed WHSV=10 over 1.1 g of the catalyst of Example 5 at 400° C. The conversion of toluene was 39.2% and the yield of p-xylene in xylenes as 29.2%.

EXAMPLE 7

[Preparation of P-ZSM-5]

Two hundred grams of NH$_4$.ZSM-5 (65 wt.% on alumina) were added to a solution of 80 grams of $(NH_4)_2HPO_4$ in 300 ml of water at about 90° C. and allowed to stand at 90° C. for 2 hours. After filtration and drying, the catalyst was calcined at 500° C. for 2 hours, yielding a P-ZSM-5 containing 3.43 wt.% phosphorus.

EXAMPLE 8A

[Alkylation reaction with the P-modified zeolite]

Alkylation of toluene with methanol was carried out by passing a toluene/methanol mixture in a molar ratio of 4/1 through 5.0 g of the catalyst of Example 7 while heating at the desired temperature. The feed weight hourly space velocity was 10. The results obtained at the various temperatures are shown below.

| Temperature °C. | Percent toluene conversion | Percent para-xylene in xylenes |
| --- | --- | --- |
| 400 | 43.6 | 66.6 |
| 450 | 54.4 | 57.7 |
| 500 | 70.4 | 53.7 |
| 550 | 85.2 | 52.0 |
| 600 | 85.2 | 58.0 |

EXAMPLE 8B

In a similar manner, alkylation of toluene with ethylene was accomplished by passing toluene and ethylene over the catalyst at a weight hourly space velocity at 7.0 and 0.5, respectively, and at 400° C. Conversion of toluene was 74.8% and selectivity to p-ethyltoluene was 55.5%.

EXAMPLE 9

[Disproportionation reaction with the P-modified zeolite]

Disproportion of toluene was carried out by passing toluene over 5.0 g of the catalyst of Example 7 at a weight hourly space velocity of 3.5 and a temperature of between 475° C. and 550° C. The conditions and results are shown below.

| Temperature | Toluene | Selectivity, mole % | | Para in |
|---|---|---|---|---|
| °C. | conversion % | Benzene | Xylene | xylenes |
| 475 | 14.9 | 52.8 | 47.6 | 39.1 |
| 500 | 27.1 | 53.3 | 45.4 | 35.1 |
| 525 | 37.4 | 56.1 | 42.2 | 32.1 |
| 550 | 44.0 | 60.4 | 37.3 | 30.1 |

EXAMPLE 10

[Preparation of Cr-P-ZSM-5]

To a solution of 5.0 g chromium acetate in 10 ml water at 80° C. was added 6.0 g of the P-ZSM-5 catalyst of Example 7. The mixture was maintained at 80° C. for 2 hours. After filtration and drying at 90° C. air, the catalyst was calcined at 500° C. for 2 hours to yield 6.1 g of Cr-P-ZSM-5. Analysis showed the content of phosphorus to be 3.21% and that of chromium to be 4.47%.

EXAMPLE 11

[Alkylation reaction with the Cr-P-modified zeolite]

Toluene was alkylated with ethylene by passing a toluene/ethylene feed stream [WHSV of 7.0 and 0.5, respectively] over 5.0 g of the Cr-P-ZSM-5 catalyst of Example 10 at 400° C. Conversion of toluene was 75.1% and selectivity to p-ethyltoluene was 62.6%.

EXAMPLE 12

[Disproportionation reaction with the Cr-P-modified zeolite]

Disproportionation of toluene was carried out by passing toluene over 5.0 g of the Cr-P-ZSM-5 catalyst of Example 10 at a weight hourly space velocity of 3.5 and a temperature of 550° C. Toluene conversion was 25.5% and the yield of the para-isomer was 32.5%.

EXAMPLE 13

[Preparation of Mo-P-ZSM-5]

To a solution of 5.0 g ammonium molybdate in 10 ml water at 80° C. was added 6.0 g of the P-ZSM-5 catalyst of Example 7 and the mixture maintained at 80° C. for 2 hours. After filtration and drying at 90° C. in air, the catalyst was calcined at 500° C. for 2 hours to yield 8.75 g of Mo-P-ZSM-5. Analysis showed the content of the phosphorus to be 2.70% and that of molybdenum to be 20.7%.

EXAMPLE 14A

[Alkylation reaction with the Mo-P-modified zeolite]

Alkylation of toluene with methanol was carried out by passing a toluene/methanol mixture in a molar ratio of 4 at a space hourly velocity at 10 through 5.0 g of the Mo-P-ZSM-5 catalyst of Example 13 while heating to the desired temperature. The results obtained at the various temperatures are shown below.

| Temperature °C. | Percent toluene conversion | Percent para-xylene in xylenes |
|---|---|---|
| 400 | 31.2 | 78.1 |
| 500 | 34.4 | 68.8 |
| 600 | 42.0 | 66.7 |

EXAMPLE 14B

Ethylation of toluene was carried out by passing toluene at WHSV=7 and ethylene at WHSV=0.5 over the Mo-P-ZSM-5 catalyst of Example 13. The temperature was maintained at 400° C. Conversion of toluene was 57.1% and the yield of p-ethyltoluene in ethyltoluene was 86.6%.

EXAMPLE 15

[Disproportionation reaction with the Mo-P-modified zeolite]

Disproportionation of toluene was accomplished by passing toluene over 5.0 g of the Mo-P-ZSM-5 catalyst of Example 13 at a WHSV of 3.5 and a temperature between 475° C. and 550° C. The conditions and the results are shown below.

| Temperature | Toluene | % Selectivity, mole | | % para in |
|---|---|---|---|---|
| °C. | conversion % | Benzene | Xylene | xylenes |
| 475 | 15.7 | 55.3 | 44.2 | 60.0 |
| 500 | 21.9 | 55.4 | 44.4 | 59.1 |
| 525 | 25.1 | 56.0 | 43.6 | 57.7 |
| 550 | 24.7 | 56.0 | 43.4 | 62.0 |

EXAMPLE 16

[Preparation of W-P-ZSM-5]

To a solution of 12.0 g of ammonium tungstate in 20 ml water at 80° C. was added 12.0 g of the P-ZSM-5 catalyst of Example 7. The mixture was maintained at 80° C. for 2 hours. After filtration and drying at 90° C. in air, the catalyst was calcined at 500° C. to yield 14.5 g of W-P-ZSM-5. Analysis indicated that the content of phosphorus was 2.90% and that of tungsten was 13.1%.

EXAMPLE 17A

[Alkylation reaction with the W-P-modified zeolite]

Alkylation of toluene with methanol was carried out by passing a toluene/methanol mixture [molar ratio of 4/1] at a WHSV=10 through 5.0 g of the W-P-ZSM-5 catalyst of Example 16 while heating at the desired temperature. The results are listed below.

| Temperature °C. | Percent toluene conversion | % para-xylene in xylenes |
|---|---|---|
| 400 | 34.8 | 72.0 |
| 500 | 59.2 | 63.3 |

EXAMPLE 17B

Ethylation of toluene was carried out in a similar manner as above by passing toluene (WHSV=7.0) and ethylene (WHSV=0.5) over the catalyst. Conversion of toluene was 70.1% and the yield of p-ethyltoluene in ethyltoluene was 72.5%.

EXAMPLE 18

[Disproportionation reaction with the W-P-modified zeolite]

Disproportionation of toluene was accomplished by passing toluene over 5.0 g of the W-P-ZSM-5 catalyst of Example 16 at 475°–550° C. and a WHSV of 3.5. The conditions and the results are shown below.

| Temperature | % Toluene | % Selectivity, mole | | % para in |
|---|---|---|---|---|
| °C. | conversion | Benzene | Xylene | xylenes |
| 475 | 12.3 | 51.8 | 47.6 | 44.9 |
| 500 | 18.8 | 51.6 | 47.5 | 43.3 |
| 525 | 26.1 | 53.5 | 45.3 | 42.0 |
| 550 | 33.3 | 56.8 | 41.7 | 40.4 |

EXAMPLE 19

Disproportionation of toluene over unmodified HZSM-12 zeolite was carried out by passing the toluene at WHSV=3.5 over 5.0 g of the catalyst in a Quartz reactor heated to between 400°–550° C. The conditions and results are summarized in the table below.

| Temperature °C. | Toluene conversion mole % | % Selectivity, mole | | % para-xylene in xylenes |
|---|---|---|---|---|
| | | Benzene | Xylene | |
| 400 | 13.9 | 50.7 | 48.1 | 25.0 |
| 500 | 42.6 | 53.7 | 41.4 | 24.3 |
| 550 | 42.6 | 55.3 | 40.5 | 24.3 |

EXAMPLE 20

Alkylation of toluene with methanol over HZSM-12 was carried out by passing a mixture of toluene/methanol (molar ratio of 4 to 1) at WHSV=10 over 5.0 g of the catalyst at the desired temperature. The results are listed below.

| Temperature °C. | Percent toluene conversion | Percent para-xylene in xylenes |
|---|---|---|
| 400 | 73.2 | 23.1 |
| 500 | 92.8 | 24.7 |

EXAMPLE 21

Alkylation of toluene with ethylene was carried out by passing toluene at WHSV=7.0 and ethylene at WHSV=0.5 over 5.0 g of HZSM-12 heated at the desired temperature. The results are listed below.

| Temperature °C. | Percent toluene conversion | Percent para-ethyltoluene in ethyltoluene |
|---|---|---|
| 300 | 4.6 | 37.2 |
| 400 | 19.3 | 30.3 |

EXAMPLE 22

[Preparation of W-P-ZSM-12]

To a solution of 3.0 g $(NH_4)_2HPO_4$ in 10 ml water at 70° C. was added 6.0 g HZSM-12. The mixture was kept at 70°–80° for 2 hours. After filtration and drying at 90° C., the catalyst was calcined at 500° C. for 2 hours to yield 6.6 g of P-ZSM-12. The phosphorus content was analyzed to be 4.78%.

To a solution of 10 g $(NH_4)_6H_2W_{12}O_4$ in 10 ml water at 80° C. was added the P-ZSM-12 zeolite and the mixture maintained at 80°–90° C. After filtration and drying at 90° C. it was calcined to give 9.7 g of W-P-ZSM-12. Analysis showed the content of phosphorus to be 2.58% and that of tungsten to be 20.5%.

EXAMPLE 23

Disproportionation of toluene was carried out by passing toluene over 5.0 g of the W-P-ZSM-12 catalyst of Example 22 at WHSV=3.5 and a temperature of 500° C. Toluene conversion was 5.6% and the yield of p-xylene in xylenes was 32.9%.

EXAMPLE 24

Alkylation of toluene with methanol was carried out by passing a mixture of toluene/methanol (molar ratio of 4/1) at WHSV of 10 and a temperature of 500° C. over the W-P-ZSM-12 zeolite of Example 22. Toluene conversion was 21.2% and the p-xylene in xylenes was 45.5%.

EXAMPLE 25

Alkylation of toluene with ethylene was carried out by passing toluene (at WHSV=7.0) and ethylene at (WHSV=0.5) at 400° C. over the W-P-ZSM-12 catalyst of Example 22. Toluene conversion was 16% and the p-xylene in xylenes was 33.8%.

The foregoing examples will clearly demonstrate the improvement to be gained by modification of the zeolite catalyst with Group VIA metals, with or without additional modification with phosphorus. It is to be understood, of course, that these examples are intended to be illustrative of certain specific embodiments of the disclosed invention. As those of skill in the art will readily appreciate, there are many variations which may be made on these specific embodiments without departing from the spirit of the invention and such variations are clearly to be encompassed within the ambit of the following claims.

What is claimed is:

1. A process for conversion of organic compounds, said process comprising contacting said organic compounds with a crystalline zeolite catalyst at a temperature of between about 250° C. and about 750° C. and a pressure within the approximate range of $10^5$ N/m² to $10^7$ N/m², said zeolite being characterized by a silica to alumina mole ratio of at least 12 and a constraint index within the approximate range of 1 to 12, said zeolite having undergone prior modification by treatment with compounds containing one or more of the elements comprising the Group VIA metals, to deposit thereon at least 0.25 weight percent of such element.

2. The process of claim 1 wherein said temperature is between 300° C. and 650° C.

3. The process of claim 1 wherein said element is chosen from the group consisting of chromium, molybdenum and tungsten.

4. The process of claim 1 wherein said element is chromium.

5. The process of claim 4 wherein said chromium comprises between 1 and 20 weight percent of the modified zeolite catalyst.

6. The process of claim 1 wherein said element is molybdenum.

7. The process of claim 6 wherein said molybdenum comprises between 1 and 30 weight percent of the modified zeolite catalyst.

8. The process of claim 1 wherein said element is tungsten.

9. The process of claim 8 wherein said tungsten comprises between 2 and 30 weight percent of the modified zeolite catalyst.

10. The process of claim 1 wherein said zeolite is also modified by treatment thereof with a compound of the element phosphorus, to deposit thereon at least 0.25 weight percent of the phosphorus.

11. The process of claim 10 wherein said zeolite has deposited thereon both phosphorus and chromium.

12. The process of claim 10 wherein said zeolite has deposited thereon both phosphorus and molybdenum.

13. The process of claim 10 wherein said zeolite has deposited thereon both phosphorus and tungsten.

14. The process of claim 1 wherein said zeolite is admixed with a binder therefor.

15. The process of claim 1, 2, 3, 4, 5, 6, 7, 8, 9, 10, 11, 12, 13 or 14 wherein said conversion comprises the alkylation of an aromatic compound by contacting said compound with an alkylating agent to produce dialkylbenzene compounds wherein the 1,4-dialkylbenzene isomer is present in excess of its normal equilibrium concentration.

16. The process of claim 15 wherein said zeolite is chosen from the group consisting of ZSM-5, ZSM-11, ZSM-12, ZSM-23, ZSM-35, ZSM-38 and ZSM-48.

17. The process of claim 15 wherein said zeolite is ZSM-5.

18. The process of claim 15 wherein said zeolite is ZSM-12.

19. The process of claim 1, 2, 3, 4, 5, 6, 7, 8, 9, 10, 11, 12, 13 or 14 wherein said conversion comprises the transalkylation of aromatic compounds to produce dialkylbenzene compounds wherein the 1,4-dialkylbenzene isomer is present in excess of its normal equilibrium concentration.

20. The process of claim 19 wherein said zeolite is chosen from the group consisting of ZSM-5, ZSM-11, ZSM-12, ZSM-23, ZSM-35, ZSM-38 and ZSM-48.

21. The process of claim 19 wherein said zeolite is ZSM-5.

22. The process of claim 19 wherein said zeolite is ZSM-12.

23. The process of claim 1, 2, 3, 4, 5, 6, 7, 8, 9, 10, 11, 12, 13 or 14 wherein said conversion comprises disproportionation of alkylbenzenes to produce benzene and dialkylbenzenes in which the proportion of 1,4-dialkylbenzene isomer is in excess of its normal equilibrium concentration.

24. The process of claim 23 wherein said zeolite is chosen from the group consisting of ZSM-5, ZSM-11, ZSM-12, ZSM-23, ZSM-35, ZSM-38 and ZSM-48.

25. The process of claim 23 wherein said zeolite is ZSM-5.

26. The process of claim 23 wherein said zeolite is ZSM-12.

* * * * *